United States Patent
Lee et al.

(10) Patent No.: US 11,091,420 B2
(45) Date of Patent: Aug. 17, 2021

(54) METHOD FOR PRODUCING FERULIC ACID FROM CORN BRANS IN HIGH PURITY AND HIGH YIELD

(71) Applicant: CJ Cheiljedang Corporation, Seoul (KR)

(72) Inventors: Joo Hang Lee, Gyeonggi-do (KR); Young Ho Hong, Gyeonggi-do (KR); Ji Hyun Kang, Seoul (KR); Hwa Jeong Lee, Gyeonggi-do (KR); Min Hoe Kim, Incheon (KR); Seung Won Park, Gyeonggi-do (KR); Seong Jun Cho, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 357 days.

(21) Appl. No.: 16/062,562

(22) PCT Filed: Oct. 21, 2016

(86) PCT No.: PCT/KR2016/011924
§ 371 (c)(1),
(2) Date: Jun. 14, 2018

(87) PCT Pub. No.: WO2017/104961
PCT Pub. Date: Jun. 22, 2017

(65) Prior Publication Data
US 2019/0077741 A1    Mar. 14, 2019

(30) Foreign Application Priority Data

Dec. 14, 2015    (KR) .................. 10-2015-0177979

(51) Int. Cl.
| | |
|---|---|
| *C07C 59/68* | (2006.01) |
| *C07C 51/47* | (2006.01) |
| *C07C 59/64* | (2006.01) |
| *C07C 59/13* | (2006.01) |
| *B01J 20/20* | (2006.01) |
| *C07C 51/42* | (2006.01) |
| *B01D 17/00* | (2006.01) |
| *C07C 51/48* | (2006.01) |
| *C07C 51/43* | (2006.01) |
| *C12P 7/42* | (2006.01) |
| *C08B 30/04* | (2006.01) |

(52) U.S. Cl.
CPC ............. *C07C 59/68* (2013.01); *B01D 17/00* (2013.01); *B01J 20/20* (2013.01); *C07C 51/42* (2013.01); *C07C 51/43* (2013.01); *C07C 51/47* (2013.01); *C07C 51/48* (2013.01); *C07C 59/13* (2013.01); *C07C 59/64* (2013.01); *C12P 7/42* (2013.01); *C08B 30/044* (2013.01); *C12Y 302/0102* (2013.01)

(58) Field of Classification Search
CPC ......... C07C 59/64; C07C 51/42; C07C 51/43; C07C 51/47; C07C 51/48; C07C 59/13; C07C 59/68; B01D 17/00; B01J 20/20; C08B 30/044; C12P 7/42; C12Y 302/0102; C23C 14/14; C23C 14/24; C23C 14/26

See application file for complete search history.

(56) References Cited

U.S. PATENT DOCUMENTS

| | | | |
|---|---|---|---|
| 6,147,206 A | 11/2000 | Doner et al. | |
| 2016/0145183 A1 | 5/2016 | Revelant et al. | |

FOREIGN PATENT DOCUMENTS

| | | | |
|---|---|---|---|
| CN | 103664580 A | | 3/2014 |
| JP | 01-242530 A | | 9/1989 |
| JP | 2000509760 T2 | | 8/2000 |
| JP | 2013220067 A2 | | 10/2013 |
| KR | 1004133840000 A | | 1/2004 |
| WO | 199840413 A1 | | 9/1998 |
| WO | 2014187784 A1 | | 11/2014 |

OTHER PUBLICATIONS

Zhao S, et al "Preparation of ferulic acid from corn bran: Its improved extraction and purification by membrane separation" Food and Bioproducts Processing Jul. 2014, 92(3):309-313; doi: 10.1016/j.fbp.2013.09.004. (Year: 2014).*
Ou S, et al "Separation and purification of ferulic acid in alkaline-hydrolysatefrom sugarcane bagasse by activated charcoal adsorption/ anion macroporous resin exchange chromatography" J. Food Eng., 2007 (ePub Feb. 21, 2006), 78, 1298-1304 ;doi: 10.1016/j.jfoodeng. 2005.12.037. (Year: 2006).*
Extended European Search Report for related European Application No. 16875903.3, dated Jul. 15, 2019 (16 pages).
Database CAPLUS [Online] Chemical Abstracts Service, Columbus, Ohio, US; Dec. 31, 2007, Luo, Y.; Ou, S.: "Studies on preparation of ferulic acid from maize bran by alkaline hydrolysis," XP002792637, Database accession No. 2008:1227726 & Luo, Y; Ou, S.: "Studies on preparation of ferulic acid from maize bran by alkaline hydrolysis," Zhongguo Shipin Xuebao, vol. 7, No. 5, Dec. 31, 2007, pp. 97-101 (Abstract, 1 page).

(Continued)

*Primary Examiner* — Aaron J Kosar
(74) *Attorney, Agent, or Firm* — Carl A. Morales; Todd K. Macklin; Dechert LLP

(57) ABSTRACT

The present disclosure relates to a series of preparation methods including extraction, separation, purification, and commercialization of ferulic acid, which is a highly functional material from corn brans (a by-product of grain), and more specifically, to a preparation method wherein ferulic acid is extracted from corn brans (a by-product of grain) in high yield by a novel method, and the extracted ferulic acid is separated and purified in high yield and high purity by an economical method, followed by commercialization.

19 Claims, 5 Drawing Sheets

(56) References Cited

OTHER PUBLICATIONS

Buranov et al., 2009, "Extraction and purification of ferulic acid from flax shives, wheat and corn bran by alkaline hydrolysis and pressurised solvents," Food Chem. 115(4):1542-1548.

Kaur et al., 2013, "Biotechnological and molecular approaches for vanillin production: a review," Appl Biochem Biotechnol. 169(4):1353-1372.

Lee et al., 1997, "Fixed-bed Adsorption of Phenolic Acids on Charcoal in Multi Solutes System," Agric Res Bull Kyungpook Natl Univ. 15:83-91.

Sgarbossa et al., 2015, "Ferulic Acid: A Hope for Alzheimer's Disease Therapy from Plants," Nutrients 7 (5):5764-5782.

\* cited by examiner

1. Alkali extraction
2. Extraction after treatment with glucoamylase for 1 hour
3. Extraction after treatment with α-amylase for 3 hours and glucoamylase for 3 hours
4. Extraction after treatment with α-amylase for 1 hour and glucoamylase for 1 hour

METHOD FOR PRODUCING FERULIC ACID FROM CORN BRANS IN HIGH PURITY AND HIGH YIELD

CROSS-REFERENCE TO RELATED APPLICATIONS

This application is a National Stage application under 35 U.S.C. § 371 of International Application No. PCT/KR2016/011924, filed Oct. 21, 2016, which claims the benefit under 35 U.S.C. § 119 of Korean Patent Application No. 10-2015-0177979, filed Dec. 14, 2015, the contents of all of which are incorporated herein in their entireties by reference thereto.

TECHNICAL FIELD

The present disclosure relates to a method for preparing ferulic acid, which is a highly functional material, from corn brans (a by-product of grain), and more specifically, to a preparation method in which ferulic acid is extracted from corn brans (a by-product of grain) in high yield by a novel method, and the extracted ferulic acid is separated and purified in high yield and high purity by an economical method, followed by commercialization.

BACKGROUND ART

Ferulic acid, which is a natural antioxidant and ultraviolet-absorbing material and skin-whitening material, is currently being investigated for entry into the global market. Due to clinical reports on its functional role of inhibiting beta-amyloid accumulation, ferulic acid has also been highlighted as a material for treating Alzheimer's disease (*Nutrients*, 2015, 7 (7): 5764 to 5782). Additionally, due to its high demand as a raw material for vanilla spices (vanillin), ferulic acid is considered to have a very high functionality and growth potential (*Appl Biochem Biotechnol*, 2013, 169 (4): 1353 to 1372).

Commercial ferulic acid has conventionally been prepared into products by performing a series of processes of separation and purification using the by-products refined during the preparation of rice bran oil (i.e., a soap in refined original oil) as a raw material in the presence of a solvent (e.g., isopropyl alcohol (IPA), hexane, ethanol, etc.) so as to obtain high-purity (98% or higher) ferulic acid. This technology was first patented by Tsuno Ltd. (a Japanese rice processing company) in 1992 (Korean Patent No. 10-0095539), and ferulic acid is now manufactured using this technology and is commercially available.

This technology employs a reasonable engineering method for the utilization of by-products of rice bran oil, but there is still a limit with regard to the industrial mass production of ferulic acid. That is, no free market structure is available for the production and sales of rice bran oil, and the raw materials are readily available only to rice bran oil manufacturers. Therefore, this technology has a significant disadvantage in market expansion through commercial enlargement of the base of ferulic acid.

Corn brans, which are obtained as a by-product in the process of producing corn starch, contain large amounts of indigestible polysaccharides and ash, and are thus not utilized in high value-added industries but are mostly used by adding to feeds. Meanwhile, ferulic acid is present as a polyphenolic component in lignin in grains and the content of corn brans in grains is in the range of 2.6% to 3.3%, which is greater than the 0.9% level in rice bran. Accordingly, the technology to extract and purify ferulic acid, an expensive physiologically active material, from unutilized corn brans is very useful and indispensable from the aspect of development of functional new materials.

Ferulic acid does not exist in grains in a free form, which is easy to extract, but it exists in a form strongly bound via an ester linkage to arabinoxylan, which is a cell wall component, as described above. For this reason, the separation of ferulic acid from grains generally requires a very complex process, and the economical production of ferulic acid is difficult due to very low yield. Additionally, ferulic acid is extracted with low purity because it is contained in a trace amount in the dry weight of corn brans, and it is extremely difficult to separate and purify ferulic acid with high purity (98% or more).

DISCLOSURE

Technical Problem

To overcome the above problems, the inventors of the present disclosure have made efforts to prepare ferulic acid from corn brans, which is an economical raw material of grain, in high yield and high purity. As a result, they have confirmed that ferulic acid can be prepared with high purity in the most effective and economical manner by performing extraction, separation, and purification processes through a novel method, thereby completing the present disclosure.

Technical Solution

An object of the present disclosure is to provide a method for preparing ferulic acid, which includes (a) reacting corn brans with an alkali solution to obtain a crude extract containing ferulic acid; (b) removing starch from the crude extract obtained in step (a); and (c) washing the extraction residue of the corn brans.

Another object of the present disclosure is to provide ferulic acid prepared by the above method.

Advantageous Effects of the Invention

The preparation method of ferulic acid of the present disclosure can economically produce ferulic acid, a high value-added material, using corn brans as a raw material, and more specifically, the preparation method of the present disclosure can produce high-purity ferulic acid in high yield, and thus can be effectively used for large-scale production of ferulic acid.

BRIEF DESCRIPTION OF DRAWINGS

FIG. 6A shows a purity evaluation of standard products of ferulic acid and FIG. 6B shows a purity evaluation of ferulic acid products prepared from corn brans.

BEST MODE

Figure 1:
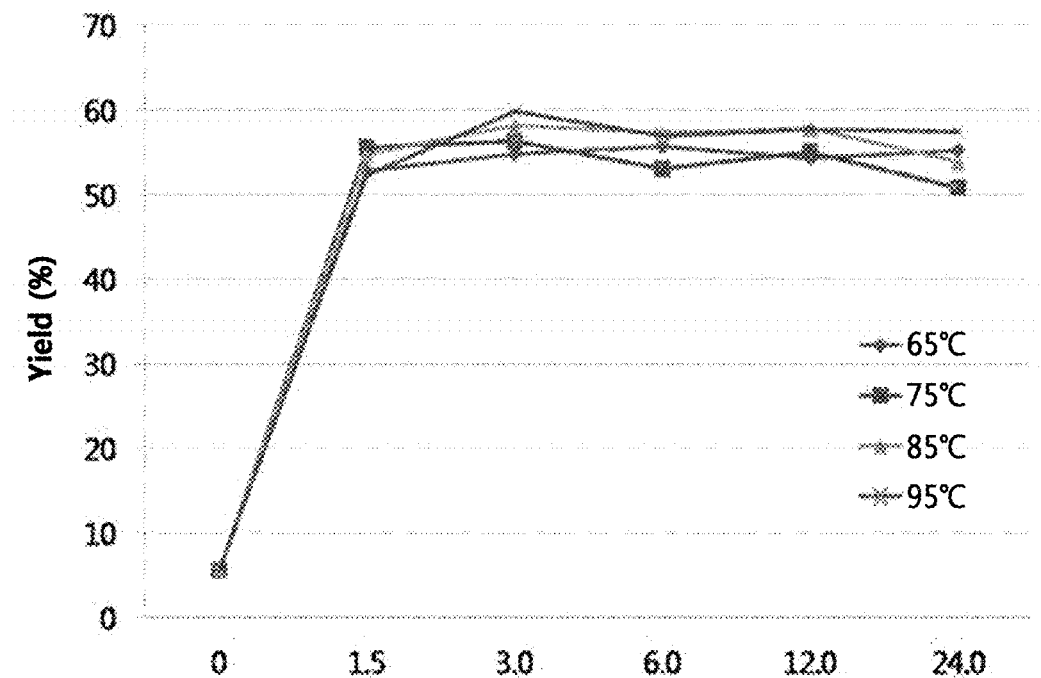
FIG. 1 shows the change in extraction yield of ferulic acid according to temperature.

To achieve the above objects, an aspect of the present disclosure provides a method for preparing ferulic acid, which includes (a) reacting corn brans with an alkali solution to obtain a crude extract containing ferulic acid; (b) removing starch from the crude extract obtained in step (a); and (c) washing the extraction residue of the corn brans.

In the present disclosure, to establish an optimal process for the preparation of ferulic acid from corn brans, which is an economical raw material of grain, ferulic acid was extracted, separated, and purified under various conditions, and the results were compared and evaluated, thereby developing an optimal method for preparing ferulic acid in high purity and high yield.

In the present disclosure, "ferulic acid", a material first extracted from plant resin in 1866, is also named hydroxycinnamic acid, 3-(4-hydroxy-3-methoxyphenyl)-2-propenoic acid, etc. and has the structure of Formula 1 below.

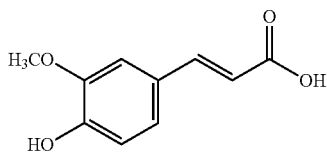

Formula 1

Ferulic acid has been reported to have effects, such as antioxidant properties, ultraviolet absorption, anti-Alzheimer activity, etc., and thus is considered as a high value-added compound that can be used in various fields. However, there is a need for the development of an economical method for preparing ferulic acid in high purity. Accordingly, the present inventors have prepared ferulic acid in high purity and with high efficiency using corn brans (i.e., a by-product of grain), which is an easily obtained raw material having a higher ferulic acid content compared to rice bran oil, which has conventionally been used as a raw material for producing ferulic acid.

Hereinafter, the method for preparing ferulic acid of the present disclosure will be described in detail.

Step (a) relates to reacting corn brans with an alkali solution to obtain a crude extract containing ferulic acid.

As used herein, the term "corn brans" refers to the outer part of the corn. Corn brans can be obtained as a by-product in the process of producing corn starch and have an advantage in that they are a cheap raw material for preparing ferulic acid and are easy to obtain. In the present disclosure, the corn brans may be obtained as a by-product in the course of processing corn or may be directly separated from corn for the production of ferulic acid, but the method of obtaining corn brans is not particularly limited as long as ferulic acid can be produced by the preparation method of the present disclosure.

In the method for preparing ferulic acid of the present disclosure, a crude extract containing ferulic acid is first obtained from corn brans. In particular, the present disclosure is characterized in that a crude extract is obtained by alkaline extraction, and this can be performed by reacting corn brans with an alkaline solution. According to an embodiment of the present disclosure, alkali extraction can show a significantly high level of ferulic acid extraction yield compared to hot-water extraction, acid extraction, and enzyme extraction.

The kind of solvent for alkali extraction is not particularly limited, but any alkali solvent suitable for extracting ferulic acid under a basic condition may be used. Specifically, the alkali solvent may be sodium hydroxide or potassium hydroxide, but the alkali solvent is not limited thereto, and one of ordinary skill in the art can select an appropriate solvent in consideration of the extraction yield of ferulic acid, solvent price, etc. Additionally, the alkali solution may be used at a concentration of 0.5% (w/w) to 1.5% (w/w), specifically 0.75% (w/w) to 1.25% (w/w), and more specifically 1% (w/w), but the concentration of the alkali solution is not limited thereto.

Alkali extraction may be performed by reacting corn brans with an alkali solution after mixing them well. Specifically, a crude extract may be obtained by mixing the corn brans with an alkali solution in a solid-liquid ratio of 1:3 to 1:15 followed by reacting them at 60° C. to 100° C. for 1 to 24 hours, more specifically by mixing the corn brans with an alkali solution in a solid-liquid ratio of 1:5 to 1:10 followed by reacting them at 65° C. to 95° C. for 1.5 to 24 hours, and most specifically by mixing the corn brans with an alkali solution in a solid-liquid ratio of 1:7 followed by reacting them at 75° C. for 2 hours, but the methods of obtaining a crude extract are not limited thereto.

Additionally, step (a) may further include filtering the crude extract obtained by the above reaction so as to remove solids.

Step (b) relates to removing starch from the crude extract obtained in step (a).

In the present disclosure, corn brans may be a by-product generated from the corn starch removal process, and thus residual starch may be present therein. If starch causes viscosity during a process, it may cause deterioration of efficiency in the process of recovering the extract and in the subsequent separation and purification process. Accordingly, a starch removal process may be performed so as to maximize the extraction yield.

The starch removal process may be performed particularly through an enzyme reaction, and specifically through an enzyme reaction in which the crude extract obtained in step (a) is reacted with α-amylase, glucoamylase, or both α-amylase and glucoamylase, but the starch removal process is not limited thereto.

The α-amylase and glucoamylase refer to enzymes that catalyze the hydrolysis of starch to glucose, and through these enzyme reactions, residual starch present in the crude extract can be removed.

The glucoamylase and α-amylase may be used specifically at a concentration of 0.1% (w/w) to 1.00% (w/w), and more specifically at a concentration of 0.5% (w/w) to 1.0% (w/w), but the concentrations of glucoamylase and α-amylase are not limited thereto and the enzyme concentration, reaction temperature, and reaction time may be appropriately selected by one of ordinary skill in the art as long as starch can be effectively removed from the crude extract.

The viscosity of a crude extract can be improved by the starch removal process, and through the process, the recovery rate of an extract can be improved, and the efficiency of the separation and purification process (i.e., a post-extraction process) can be improved.

Step (c) relates to washing extraction residues of corn brans, and this step is for obtaining higher extraction yield through residue washing in consideration of the extraction characteristics of solid raw materials.

The residue washing may be performed using 1 to 10 volumes of water, and specifically 5 volumes of water, compared to the volume of residues of corn brans, but the water volume is not limited thereto.

The preparation method may further include separation and purification of ferulic acid. That is, high-purity ferulic acid at a level that can be commercialized can be obtained by performing processes of alkali extraction of corn brans, starch removal, and residue washing so as to extract ferulic acid in high yield, followed by separation and purification of ferulic acid.

In the present disclosure, the separation and purification process may be performed through various separation and purification processes known in the art, and particularly by a primary purification process using activated carbon and a secondary purification process using adsorption resin, but the separation and purification process is not particularly limited thereto.

Since ferulic acid is present at a very low level of less than 3% in corn brans, it is important to improve the purity in the purification process for the commercialization of ferulic acid. In this regard, the present inventors have compared various purification methods, and as a result, they have confirmed that ferulic acid can be most efficiently purified to have high purity through the primary purification process using activated carbon and the secondary purification process using an adsorption resin.

In the primary purification process using activated carbon, the activated carbon may be granular activated carbon or powdered activated carbon, but the activated carbon is not limited thereto. The activated carbon may be used at a concentration of 0.1% (w/v) to 2% (w/v), specifically at a concentration of 1% (w/v) relative to that of the extract.

The purification process using activated carbon may be performed in the order of (1) adsorption with activated carbon using the adsorption phenomenon of ferulic acid onto activated carbon, (2) hot-water washing of the activated carbon for removing organic materials other than ferulic acid, (3) desorption of the ferulic acid for the recovery of ferulic acid, and (4) pH adjustment for removing solids being precipitated according to pH.

The desorption may be performed using an alkali solvent, and the alkali solvent may specifically be sodium hydroxide or potassium hydroxide, but the alkali solvent is not limited thereto. Additionally, the alkali solvent may be used at a concentration of 0.01% (w/w) to 0.5% (w/w), and specifically at a concentration of 0.05% (w/w) to 0.1% (w/w), but the concentration of the alkali solvent is not limited thereto.

The pH adjustment step in the course of the primary purification process may be to adjust the pH of the process liquid, which was detached through the above desorption of ferulic acid, to pH 3 to 4 so as to remove impurities by precipitation.

The secondary purification process using the adsorption resin may include adsorbing the process liquid obtained from the primary purification process to an adsorption resin, and desorbing ferulic acid therefrom.

The type of adsorption resin for use may include, for example, PAD900, Mn100, HP20, PAD600, etc., but the resin is not particularly limited thereto.

The desorption of the ferulic acid adsorbed to the adsorption resin may be performed using an ethanol solvent at a concentration of 15% (w/w) to 35% (w/w), specifically 20% (w/w) to 30% (w/w), and more specifically 30% (w/w), but the concentration of ethanol solvent is not limited thereto.

Furthermore, the method for preparing ferulic acid of the present disclosure may further include crystallization of ferulic acid, which is separated and purified, so as to secure high purity for the commercialization of ferulic acid. The crystallization may be appropriately performed by one of ordinary skill in the art through a method commonly known in the art. For example, the crystallization may be performed in the order of (1) condensation of a detached fraction, (2) hot-water dissolution of precipitates, (3) crystallization by lowering temperature, and (4) recovery of ferulic acid crystals, but the crystallization process is not limited thereto.

Another aspect of the present disclosure provides ferulic acid prepared by the above method.

DETAILED DESCRIPTION OF THE INVENTION

Hereinafter, the present disclosure will be described in detail through exemplary embodiments. However, these exemplary embodiments are provided for the purpose of illustration only and are not intended to limit the scope of the present disclosure.

Example 1. Screening of Methods for Extracting Ferulic Acid from Corn Brans

To select the most effective method for extracting ferulic acid (i.e., a high value-added material) using corn brans (i.e., a by-product generated in the course of processing corn) as a raw material, extractions were performed by hot-water extraction, acid extraction, alkali extraction, and enzyme extraction, and the results were compared. The subsequent process was optimized based on the extraction method that exhibited the most excellent result throughout the process.

After the extractions, a standard analysis method was established to evaluate the content and yield of ferulic acid, and ferulic acid in each extracted solution was analyzed through the method.

The standard analysis method for ferulic acid is as follows:

(1) 100 mg each of the raw material was weighed in three cap tubes.

The water contents of raw materials were measured simultaneously and compared together with that of the genuine product of ferulic acid (Sigma, >99%) as a control group.

(2) 2 M NaOH (5 mL) each was added to each cap tube, and each cap tube was sealed with a stopper.

(3) A reaction was performed in a constant-temperature water bath at 45° C. while shaking intermittently for stirring.

It is recommended that hydrolysis be performed in each of the three tubes for 10, 20, and 40 hours, respectively. However, the hydrolysis time is flexible according to raw materials.

(4) Upon hydrolysis, the samples were vigorously stirred, allowed to stand, and about 2 mL to 3 mL of the supernatant was collected and centrifuged.

(5) After the centrifugation, the supernatant was collected and filtered with a 0.45 μm filter.

(6) The filtrate (1 mL) was collected and transferred into a tube for separation and recovery of a solvent.

(7) The recovered solvent (1 mL) was neutralized by adding 35% HCl (0.2 mL) thereto.

(8) Ethyl acetate (3 mL) was added to the neutralized solvent (1 mL), stirred, and allowed to stand, and the supernatant was recovered. The whole process was repeated 5 times in total so as to recover ferulic acid.

(9) The recovered ethyl acetate (about 15 mL) was dried in a vacuum centrifugal dryer at 60° C. to completely remove the solvent.

(10) 50% MeOH (5 mL) was added to the solids, from which the solvent was removed, to completely dissolve the solids (standard product was used with a constant volume of 250 mL).

(11) HPLC (column: Capcellpak 18) analysis was performed without dilution Additionally, the conditions for each extraction for the purpose of selecting the optimal extraction method are as follows.

(1) Acid Extraction

1% $H_2SO_4$ (1 L) was added to corn brans (100 g) and reacted at 120° C. for 1.5 hours. Then, the resultant was neutralized via $CaCO_3$ and filtered. The ferulic acid from the filtrate was analyzed by HPLC (column: Capcellpak 18). To confirm the amount of ferulic acid destroyed by acid, the standard product of ferulic acid (Sigma, >99%) was reacted under the same conditions for acid extraction (1% $H_2SO_4$, 120° C., 1.5 hours). Additionally, to identify the amount of ferulic acid destroyed by temperature, the standard product of ferulic acid (Sigma>99%) was reacted in purified sterile water at 120° C. for 1.5 hours, and thereby the destruction rate of ferulic acid was confirmed.

(2) Enzyme Extraction

Corn brans (60 g) and sterile water (300 g) were mixed well. Then, each enzyme was added thereto at a concentration of 5%, mixed, and reacted while stirring in a shaking incubator at 45° C. for 15 hours. After the reaction, the resultant was subjected to filtration to remove solid materials, and then ferulic acid from the filtrate was analyzed by HPLC.

(3) Alkali Extraction 500 mL each of 1% NaOH or 1% KOH was added to corn brans (100 g), mixed well, and reacted at 75° C. or 95° C. for 2 hours. After the reaction, the resultant was subjected to filtration to remove solid materials, and then ferulic acid from the filtrate was analyzed by HPLC.

(4) Hot-Water Extraction

Sterile water (1 L) was added to corn brans (100 g) and mixed by stirring. Then, reactions were performed at 120° C., 140° C., and 160° C. for 1 hour, respectively. The resultant was subjected to filtration to remove solid materials, and ferulic acid from the filtrate was analyzed by HPLC.

The yields of ferulic acid extracted in the corn brans were analyzed by the extraction and analysis methods described above (Table 1).

TABLE 1

Screening of extraction methods for extracting ferulic acid from corn brans

| Extraction Method | Catalyst | Raw Material (mg) | Temperature (° C.) | Time (hr) | Yield (%) |
|---|---|---|---|---|---|
| Control Group | | Ferulic acid (Sigma, >99%) | 120 | 1 | 95.67 |
| Hot-water Extraction | Vapor | Corn brans | 120 | 1 | 5.32 |
| | | Corn brans | 140 | 1 | 25.33 |
| | | Corn brans | 160 | 1 | 39.02 |
| Acid Extraction | 1% $H_2SO_4$ | Corn brans | 120 | 1.5 | 5.83 |
| Alkali Extraction | 1% NaOH | Corn brans | 75 | 2 | 55.58 |
| | 1% KOH | Corn brans | 95 | 2 | 61.61 |
| Enzyme Extraction | Shearzyme | Corn brans | 45 | 15 | — |
| | Viscozyme L | Corn brans | 45 | 15 | 3.13 |
| | Pectinex | Corn brans | 45 | 15 | 2.88 |
| | Celluclast | Corn brans | 45 | 15 | 5.15 |
| | Novarom | Corn brans | 45 | 15 | 3.42 |
| | Cytolase | Corn brans | 45 | 15 | 6.12 |
| | Sumizyme | Corn brans | 45 | 15 | 8.34 |
| | Rapidase | Corn brans | 45 | 15 | 3.34 |

As a result, the maximum yield for the hot-water extraction at 160° C. was shown to be 39%. In the case of the acid extraction, the yield was shown to be about 5.8%, but in the analysis of the destruction rate by an acid, the destruction rate was shown to be 94.17%. From these results, it was confirmed that hydrolysis of materials occurred during the acid extraction, and thus acid extraction is not a suitable extraction method for ferulic acid. The enzyme extraction was performed by purchasing commercial enzymes capable of degrading structural proteins. The ferulic acid within biomass forms a complex structure with lignin in the form of arabinoxylan. The mechanism of enzymatic degradation of the ester bond between lignin and arabinoxylan is possible through feruloylesterase. The commercial enzymes having the activity of the feruloylesterase were selected with high priority and the extraction was performed by the enzyme extraction method described above. As a result of the extractions, it was found that most of the enzymes exhibit poor extraction yields of less than 10%. The enzyme extraction alone may have the advantage of selective extraction; however, it was confirmed that the energy was not sufficient to decompose the entire ester bond between lignin and arabinoxylan. The alkali extraction was performed using 1% NaOH or 1% KOH. The extraction rates when each catalyzing agent was used were 55.6% and 61.6%, which were superior to those obtained by other extraction methods.

Therefore, the present inventors have reviewed various extraction methods and have confirmed that the alkali extraction method is the most efficient method for extracting ferulic acid from corn brans. Additionally. NaOH, which is the cheaper of the two between NaOH and KOH, was determined to be more effective, and thus NaOH was used in the subsequent tests for optimizing the extraction conditions.

Example 2. Establishment of Optimal Conditions for High-Yield Extraction of Ferulic Acid The present inventors have proceeded with the optimization for extraction conditions in consideration of securing a higher yield of ferulic acid and the efficiency of the purification process after extraction. First, in order to secure the optimal concentration of an alkali catalyzing agent and the reaction time, NaOH at various concentrations (0%, 0.5%, 0.75%, and 1%) were added to 100 g of the raw material (corn brans), respectively. When the NaOH solution was added, the solid-liquid ratio between the raw material and the solution was maintained at 1:5 and the extraction temperature was set at 95° C. Additionally, to confirm the optimal extraction, the extraction yields of ferulic acid were confirmed by sampling at each time point. As a result of confirming by the method described above, it was confirmed that the NaOH concentration suitable for the maximum extraction yield was 1%. From these results, it was confirmed that the extractions were almost completed within 1.5 to 3 hours after the extractions (Table 2).

TABLE 2

Changes in ferulic acid extraction yields according to alkali concentration and time

| Category | NaOH (0%) Extraction yield (%) | | NaOH (0.5%) Extraction yield (%) | | NaOH (0.75%) Extraction yield (%) | | NaOH (1%) Extraction yield (%) | |
|---|---|---|---|---|---|---|---|---|
| | 1st | 2nd | 1st | 2nd | 1st | 2nd | 1st | 2nd |
| 0 hr | 0.07 | 0.22 | 5.01 | 2.48 | 8.84 | 5.75 | 10.32 | 9.25 |
| 1.5 hr | 0.06 | 0.51 | 58.54 | 63.98 | 66.26 | 76.95 | 69.89 | 79.16 |
| 3 hr | 0.16 | 1.05 | 59.03 | 56.47 | 60.05 | 71.53 | 67.72 | 73.87 |
| 6 hr | 0.25 | 1.17 | 38.05 | 36.82 | 65.02 | 71.66 | 67.83 | 73.51 |

TABLE 2-continued

Changes in ferulic acid extraction yields according to alkali concentration and time

| Category | NaOH (0%) Extraction yield (%) | | NaOH (0.5%) Extraction yield (%) | | NaOH (0.75%) Extraction yield (%) | | NaOH (1%) Extraction yield (%) | |
|---|---|---|---|---|---|---|---|---|
| | $1^{st}$ | $2^{nd}$ | $1^{st}$ | $2^{nd}$ | $1^{st}$ | $2^{nd}$ | $1^{st}$ | $2^{nd}$ |
| 12 hr | 0.17 | 1.58 | 19.74 | 11.71 | 52.66 | 48.94 | 65.37 | 65.90 |
| 24 hr | 0.32 | 2.03 | 5.19 | 3.33 | 35.57 | 18.05 | 60.20 | 60.10 |

The conditions that can affect extraction yields may include a solid-liquid ratio between a raw material and an alkali solution. Accordingly, the present researchers have performed tests to confirm the optimal ratio with respect to the solid-liquid ratio between a raw material and an alkali solution. The tests were performed by setting the solid-liquid ratio between a raw material and an alkali solution at 1:5, 1:7, and 1:10, respectively, in consideration of commercial availability. As a result of the tests of solid-liquid ratios, it was confirmed that very similar yields were shown at solid-liquid ratios of 1:7 and 1:10 (Table 3).

TABLE 3

Changes in extraction yields according to solid-liquid ratios between raw material and alkali solution

| Category | Solid-Liquid Ratio (1:5) Extraction yield (%) | | Solid-Liquid Ratio (1:7) Extraction yield (%) | | Solid-Liquid Ratio (1:10) Extraction yield (%) | |
|---|---|---|---|---|---|---|
| | NaOH (0.75%) | NaOH (1%) | NaOH (0.75%) | NaOH (1%) | NaOH (0.75%) | NaOH (1%) |
| 0 hr | 8.84 | 9.25 | 4.17 | 4.11 | 4.73 | 1.45 |
| 1.5 hr | 66.26 | 79.16 | 75.24 | 83.84 | 73.85 | 77.87 |
| 3 hr | 60.05 | 73.87 | 74.57 | 81.56 | 74.26 | 79.51 |
| 6 hr | 65.02 | 73.51 | 70.23 | 81.52 | 71.83 | 76.78 |
| 12 hr | 52.66 | 65.90 | 73.12 | 75.31 | 72.05 | 83.59 |
| 24 hr | 35.57 | 60.10 | 59.40 | 77.52 | 62.01 | 83.95 |

From the above results, it can be seen that the solid-liquid ratio of 1:7, which can reduce the amount of water consumption and the amount of waste water generation, is efficient, considering commercial application.

Additionally, to confirm the effects of temperature on extraction, the effect of extraction yields in the temperature range of 65° C. to 95° C. was confirmed (FIG. 1). As a result of confirming the effects of temperature on extraction, the extraction yield distribution in the range of 65° C. to 95° C. was shown to be similar, and the extraction yields 1.5 hours after the extractions were shown to have very similar distribution, as is the case with the above results. These results suggest that 1% NaOH exhibits most of the catalytic effects necessary for extraction.

Example 3. Improvement of Extraction Yield Through Enzyme Application Technology Corn brans, which are a by-product of corn processing, are a by-product produced after the process of removing corn starch, and thus unremoved starch still remains in the raw material (corn brans). Starch provides viscosity during the process and significantly inhibits the process of recovering an extract after extraction and post-extraction processes. In this regard, the present inventors have studied methods for maximizing extraction yields by combining the technologies for alkali extraction with the enzyme technologies for removing starch. The method of the present disclosure can provide an effect of improving extraction yields and facilitating the purification process after extraction to proceed more smoothly.

To determine the effects of a starch structure within the raw material on extraction yields, α-amylase and glucoamylase used in corn processing were used. The effects of extraction were examined by setting the reaction temperature at 95° C. for α-amylase and at 65'C for glucoamylase while setting the enzyme concentration at 1%.

Figure 2:
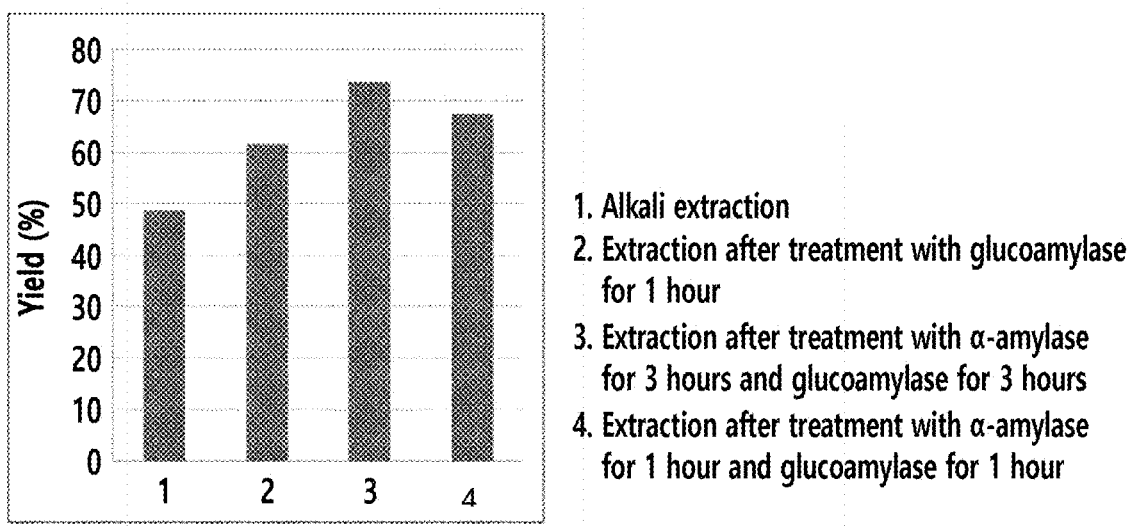
FIG. 2 shows the improvement in extraction yield of ferulic acid using enzymes.

To analyze the effects of enzyme application, four experimental groups were constructed as follows: (1) performing an alkali extraction, (2) applying glucoamylase for 1 hour and performing an extraction, (3) applying α-amylase for 3 hours, reacting with glucoamylase for 3 hours, and performing an extraction, and (4) applying α-amylase for 1 hour, reacting with glucoamylase for 1 hour, and performing an extraction. The changes in extraction yields in the above four experimental groups were confirmed (FIG. 2).

As a result of the experiments, it was confirmed that the extraction yields were significantly higher in the experimental groups where glucoamylase and α-amylase were used compared to the experimental group where only an extraction alone was performed. Additionally, it was confirmed that the combined use of glucoamylase and α-amylase was superior to the extraction using glucoamylase alone in improving extraction yield and physical properties. It is thought that this is because, as described above, the viscosity is improved by the removal of the starch component, and as a result, the recovery rate of the extract is improved. Through this process, the efficiency in the purification process, which is a post-extraction process, can be improved. Therefore, the present inventors have confirmed that the most important part in the process of extracting ferulic acid in corn brans is the combined utilization with the present enzyme technology.

Additionally, to optimize the enzyme concentration, the changes in extraction yields according to glucoamylase concentration were evaluated. Reactions were performed at glucoamylase concentrations of 0.1%, 0.5%, and 1.0% at 65° C. for 2 hours. Additionally, the extraction after glycosylation was performed in 1% NaOH (75° C.).

When the extraction yield of ferulic acid was improved, the effect of glucoamylase concentration was shown to be the same after the concentration was 0.5%. Therefore, the present inventors were able to optimize the glucoamylase concentration to improve the extraction yield of ferulic acid at 0.5%.

The yield was improved by the enzyme-treated process, and it was possible to obtain a higher extraction yield by further performing a residue washing in consideration of the extraction characteristics of solid raw materials. Therefore, the present inventors have confirmed the changes in the extraction yield through the washing of the extraction residue after the extraction. The following four experimental groups were constructed in order to confirm the effect of residue washing after extraction: (1) alkali extraction, (2) residue washing after alkali extraction, (3) glucoamylase treatment and alkali extraction, and (4) residue washing after glucoamylase treatment and alkali extraction.

Figure 4:
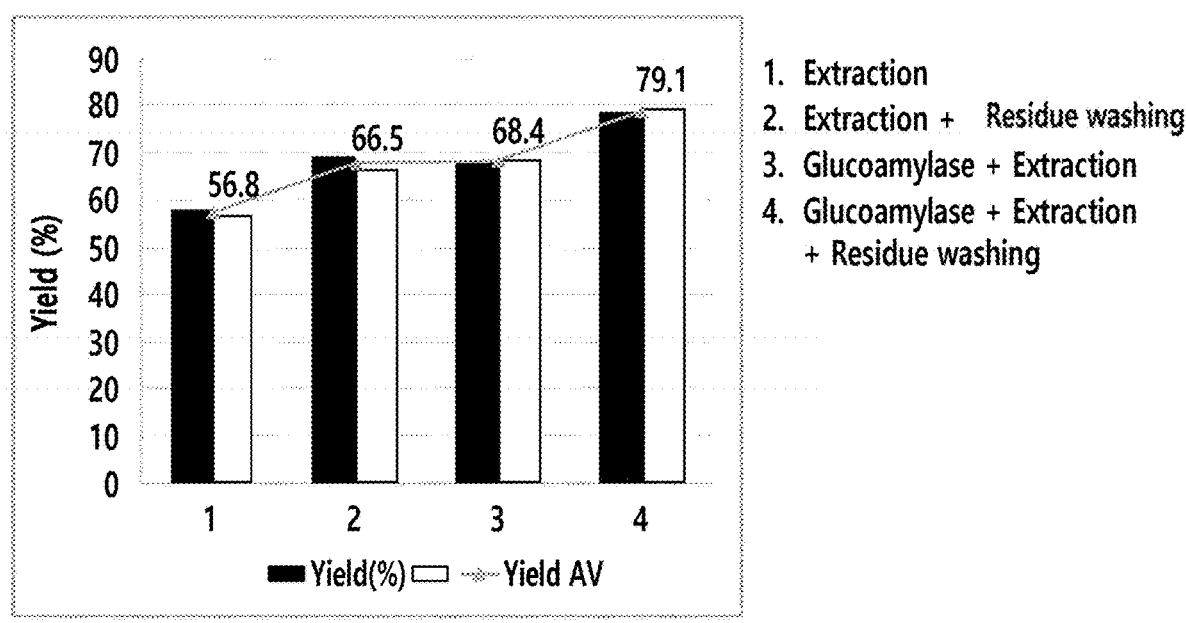
FIG. 4 shows the extraction yield according to residue washing.

As a result of the tests with the four experimental groups constructed as described above, a level of about 10% of additional ferulic acid could be secured when residue washing was performed. Additionally, as in the previous results, the experimental groups where glucoamylase was reacted showed an increase of the yield by about 13% or greater compared to those groups where glucoamylase was not reacted (FIG. 4).

Figure 5:
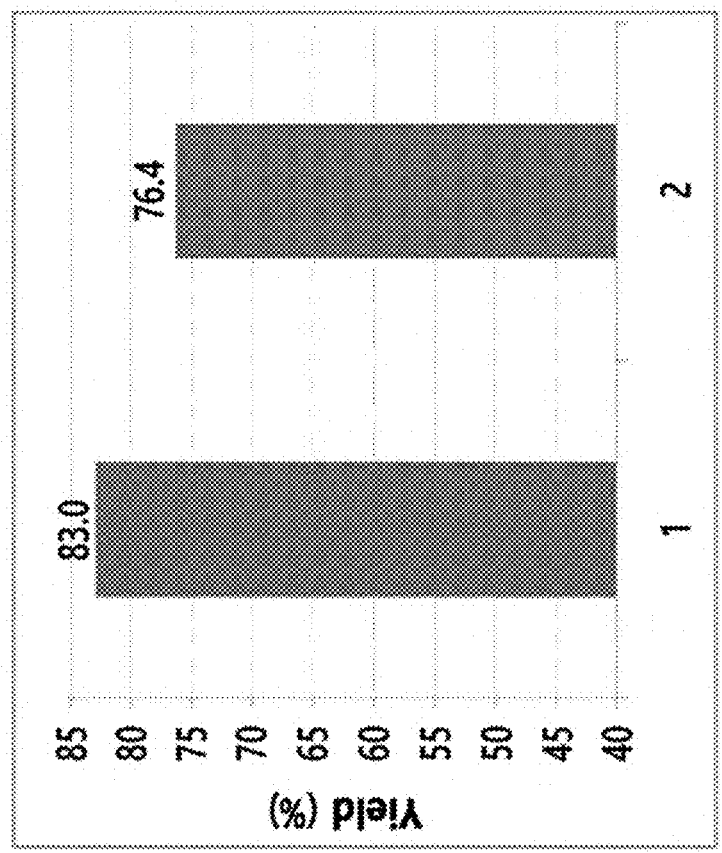
FIG. 5 shows the extraction yield according to the time of glucoamylase treatment.

Previously, it was confirmed that the enzyme technology may be used to maximize the extraction yield when ferulic acid is extracted from corn brans. In this regard, the present inventors have attempted to confirm the effects of glucoamylase before and after alkali extraction. Additionally, to improve the recovery rate after extraction, it was expected that the extraction yield will be further increased through the washing of extraction residue. For this experiment, two experimental groups were prepared as follows: (1) performing treatment with glucoamylase (0.5% glucoamylase, 65° C. for 2 hours) after alkali extraction, and washing of extraction residue (use of 5 volumes of distilled water compared to that of raw material) and (2) first, performing treatment of corn brans with glucoamylase, alkali extraction, and washing of extraction residue. Two experimental groups were prepared as such, and the extraction yields of these two experimental groups were evaluated (FIG. 5).

As a result of the experiments, it was confirmed that the experimental group where glucoamylase was treated after alkali extraction showed a higher extraction yield compared to that where glucoamylase was treated before alkali extraction. In this regard, the present inventors were able to optimize the application of glucoamylase for maximizing the extraction yield by performing the same after the alkali extraction.

Figure 3:
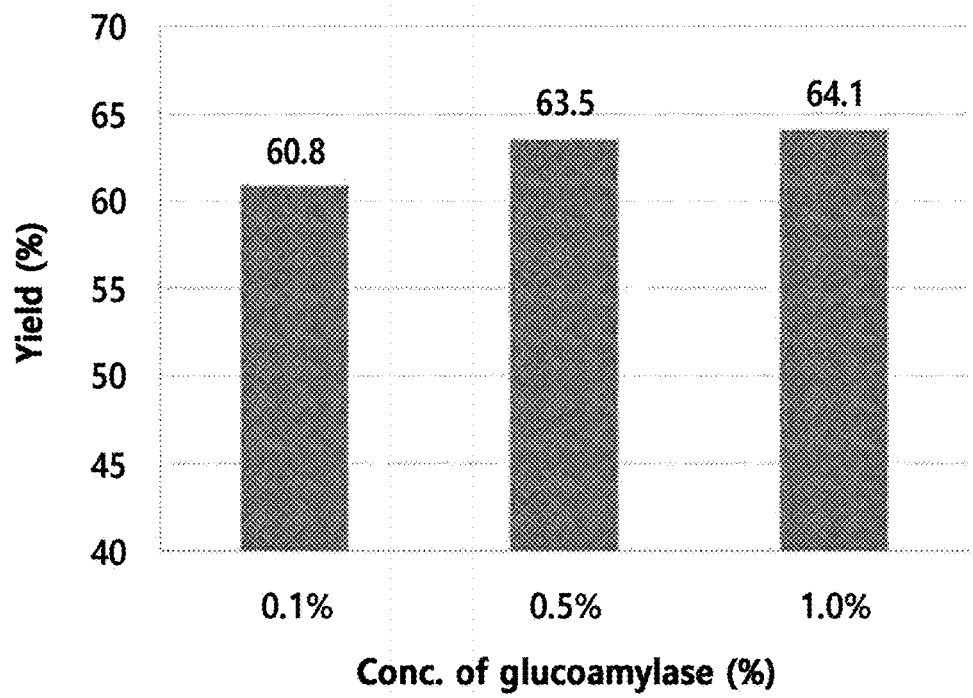
FIG. 3 shows the extraction yield according to glucoamylase concentration.

As described above, the present inventors have performed the optimization with regard to the process of extracting ferulic acid in high yield from corn brans, which are a byproduct of corn processing. Subsequently, the inventors of the present invention have performed extraction of ferulic acid based on the description above, and the development of high-purity separation and purification technology was performed using an extraction process solution. Additionally, the subsequent study for the development of a high-purity separation and purification method was performed by the optimized extraction method described below. The optimized extraction method is as follows. After performing the extraction under the conditions (a solid-liquid ratio between corn brans and water of 1:7 (Table 3), 1% NaOH (Table 2), 75° C. for 2 hours (FIG. 1)), glucoamylase in an amount of 0.5% (w/w) was added thereto (FIGS. 3 and 5) and allowed to react at 65° C. for 1 hour. After the enzyme reaction, the solid fraction was separated by filtration and used as a processing solution for the subsequent high-purity separation and purification process.

Example 4. Development of Technology for High-Purity Separation and Purification of Extracted Ferulic Acid Since ferulic acid is present in corn brans at less than 3%, it is a very difficult process to improve purity in the purification process after extraction. Accordingly, the present inventors have performed a wide variety of methods for ferulic acid purification suitable for a food-type process, and have performed studies on purification methods with the highest efficiency and high-purity.

To summarize the process for purifying the extracted ferulic acid, a purification process including a total of 6 steps with a final purity of 98% or higher was performed as shown below:

1) adsorption of activated carbon: use of the phenomenon of ferulic acid to adsorb to activated carbon;

2) hot-water washing of activated carbon: removal of organic materials other than ferulic acid;

3) desorption of ferulic acid within activated carbon: securing ferulic acid with improved purity;

4) pH adjustment: removal of solids being precipitated according to pH;

5) adsorption and desorption of adsorption resin: maximization of purity by purification; and 6) crystallization of powders: securing of products with a purity of 98% or higher.

(1) Process of Purifying Ferulic Acid Through Activated Carbon

Ferulic acid is a lignin-based organic material having a structural characteristic of being adsorbed on activated carbon. Accordingly, for the ease of purification, the present inventors have selected activated carbon under the conditions where the yields to adsorb and detach according to the type of activated carbon (granular activated carbon and powdered activated carbon) and the improvement of purity after detachment are most excellent, and have attempted to apply the selected activated carbon to the process. The ferulic acid solution extracted through the optimized extraction conditions described in Examples above was used for efficient and high-purity purification of ferulic acid.

When the ferulic acid extract in corn brans was added to activated carbon (powdered activated carbon or granular activated carbon), the adsorption rate of ferulic acid was 95% or higher. Specifically, to increase the adsorption efficiency, the activated carbon was tested using powdered activated carbon and granular activated carbon, and was adsorbed at a level of 95% to 99% in both types of activated carbon.

However, powdered activated carbon showed an excellent result during the detachment process compared to granular activated carbon, and thus, the subsequent purification of activated carbon was performed using powdered activated carbon. The adsorption can be performed at various temperature conditions, and the present inventors have ultimately performed the adsorption at room temperature. Additionally, to optimize the appropriate amount of activated carbon to be used, the amount of activated carbon used was examined at the level of 0.1% (w/v) to 2% (w/v). As a result, the appropriate amount of activated carbon was evaluated to be 1% (w/v) relative to the amount of the extract. The evaluation of a detachment solvent for the detachment of ferulic acid adsorbed within the activated carbon was confirmed according to the concentration of NaOH (0.05% to 0.5%) as an alkaline solvent, and as a result, the purity of ferulic acid within the detached solution and the yield of detachment were shown to be similar at 0.05% NaOH and 0.1% NaOH (Table 4).

To improve the purity of ferulic acid during the purification process of activated carbon, the activated carbon was washed with hot water (90° C.) to use the principle that organic materials within the activated carbon detach according to temperature after adsorption. As a result, there was an effect that about 11.6% of impurities were further removed after the hot-water wash (Table 5).

TABLE 4

| Process | Vol (mL) | FA Conc. (mg/mL) | FA Wt. (mg) | FA Yield (%) | Assay Vol (mL) | Content (Assay) Dry Wt. (mg) | Purity (%) | FA (mg) | Impurity (mg) | Impurity Removal Rate (%) |
|---|---|---|---|---|---|---|---|---|---|---|
| Extract | 50 | 0.629 | 31.45 | 100.00 | 24 | 670.0 | 2.26 | 15.17 | 654.83 | 0.00 |
| 0.05% NaOH | 35.34 | 0.357 | 12.62 | 40.12 | 25 | 85.0 | 10.32 | 8.77 | 76.23 | 11.64 |
| 0.1% NaOH | 35.4 | 0.347 | 12.28 | 39.06 | 24 | 93.0 | 8.98 | 8.36 | 84.64 | 12.93 |
| 0.5% NaOH | 36.13 | 0.469 | 16.94 | 53.88 | 25 | 180.0 | 6.40 | 11.52 | 168.48 | 25.73 |

TABLE 5

| Process | Vol (mL) | FA Conc. (mg/mL) | FA Wt. (mg) | FA Yield (%) | Assay Vol (mL) | Content (Assay) Dry Wt. (mg) | Purity (%) | FA (mg) | Impurity (mg) | Impurity Removal Rate (%) | Condition |
|---|---|---|---|---|---|---|---|---|---|---|---|
| Extract | 50 | 0.901 | 45.07 | 100.00 | 25 | 1,484.4 | 1.52 | 22.53 | 1,461.87 | 0.00 | — |
| Activated carbon-adsorbed supernatant | 47 | 0.007 | 0.31 | 0.69 | 25 | 1,068.9 | 0.02 | 0.16 | 1,068.74 | 73.11 | Powdered activated carbon 1% (w/v), Rm Temp for 1 hr, 170 rpm |
| Solution for washing activated carbon | 46 | 0.031 | 1.44 | 3.19 | 25 | 124.7 | 0.63 | 0.78 | 123.92 | 11.59 | 90° C., 30 min |
| Solution for detaching activated carbon | 47 | 0.740 | 34.78 | 71.17 | 25 | 94.2 | 19.64 | 18.50 | 75.70 | 5.18 | 0.1% NaOH (60° C., 1 hr) |
| pH Adjusting supernatant | 48 | 0.609 | 29.26 | 64.91 | 25 | 52.4 | 29.08 | 15.24 | 37.16 | 2.54 | 6N HCl neutralization (pH 3 to 4) |

This hot-water washing process facilitates the detachment of ferulic acid adsorbed to activated carbon by removing organic substances other than ferulic acid and has the effect of improving the purity after detachment.

Then, to further improve the purity of ferulic acid after purification, the present inventors have used the sedimentation effect of residual organic matters present in the extract according to pH. When the processing solution detached from the activated carbon was adjusted to have a pH of 3 to 4 using an acidic solution (HCl), a large amount of impurities was shown to be precipitated, and an additional purity increase of 10% or higher was achieved by this adjustment (Table 5). Through the effect of precipitating organic matters by lowering pH, it was possible to remove viscous materials, and the physical property that can be inputted into the subsequent adsorption resin process was secured. Additionally, through the activated carbon and the methods of improving the purity described above, the purity of ferulic acid at a level of about 2% after the extraction was innovatively improved to a level of about 30%.

Based on these results, as the conditions for the primary purification of high-purity ferulic acid, 1% (w/w) powdered activated carbon was added to an extraction filtrate, reacted at room temperature for 1 hour, adsorbed to activated carbon, and washed with hot water (90° C.) corresponding to the volume equivalent to that of the extract (Table 5), and then detached by utilizing 0.05% NaOH at a volume equivalent to that of the extract (Table 4). The detached solution was neutralized to pH 3 to 4 using 6 N HCl, and the primary purification solution was obtained by filtration (Table 5). The obtained primary purification solution was used as a solution for the absorption resin process, which is a subsequent process.

(2) Process for High-Purity Ferulic Acid Through Absorption Resin Process

The extraction purity of ferulic acid obtained from an extraction process is about 1.5% to about 2.5%, and the purity of the ferulic acid obtained from the purification process of activated carbon is about 30% (Table 5). The purity of ferulic acid that can be used as a commercial product is 98% or higher. For this purpose, the present inventors have performed a resin process and a crystallization process so as to obtain high-purity ferulic acid. The processing solution used for the resin process was one with a purity of 30%, which underwent the primary purification from the extract using activated carbon (Table 5).

The resin process was also confirmed to have the effect by the anionic resin. However, an adsorbent resin was determined to have superiority in terms of purity and yield of ferulic acid, and thus the high-purity processes were performed using a PAD900 (Purolite®) resin, which was confirmed by tests for each type of adsorption resin. The tests for the adsorption resin process were performed at room temperature, in which SV was maintained in the range of 3 to 6 at the time of adsorption and SV was maintained at 10 at the time of desorption. The total amount of the adsorption resin used in the tests was 14 mL. The concentration of ferulic acid that underwent the primary purification in activated carbon was 0.66 g/L, and the adsorption capacity was 41.5 g-FA/L-resin. As a result of the tests (20% to 80%) according to the concentration of detachment solvent (ethanol), a separation pattern of high-purity (79% to 85%) ferulic acid was observed at a low concentration of the ethanol detachment solvent. When the crystallinity of ferulic acid in each fraction was examined, the crystallinity was observed in detached ferulic acid at ethanol concentrations of 20% and 30% (Table 6).

TABLE 6

| Category | Loading Solution | Permeate Solution | Detachment Solution (EtOH, %) | | | | | | |
|---|---|---|---|---|---|---|---|---|---|
| | | | 20 | 30 | 40 | 50 | 60 | 80 | TTL |
| Total Volume (mL) | 1,000 | 1,140 | 80 | 80 | 80 | 80 | 80 | 80 | 400 |
| HPLC (g/L) | 0.6583 | 0.0675 | 1.6100 | 2.2382 | 1.8208 | 1.0605 | 0.4160 | 0.1530 | — |
| FA (g) | 658.3 | 77.0 | 0.129 | 0.179 | 0.146 | 0.085 | 0.033 | 0.012 | 0.006 |
| Dry Wt. (g) | 2.0880 | 1.2814 | 0.1625 | 0.2208 | 0.1973 | 0.1207 | 0.0519 | 0.0290 | — |
| Purity (% DS) | 32.02 | 3.55 | 79.49 | 85.59 | 80.08 | 74.18 | 68.12 | 39.44 | — |
| Crystallinity of Ferulic Acid | — | — | ○ | ○ | x | x | x | x | — |

The above results can indirectly confirm that even ferulic acid of the same purity detached at different ethanol concentrations has impurities that can inhibit the crystallinity of ferulic acid. Accordingly, the present inventors were able to optimize the concentration of ethanol, which is a detachment solvent, during the adsorption resin process.

As described above, with respect to the adsorption resin process, high-purity ferulic acid (80% level) was implemented by performing detachment with 30% ethanol after the adsorption to the PAD900 adsorption resin. The subsequent crystallinity process proceeded with reference to a processing solution with an 80% purity level, which underwent the extraction of corn brans, a primary purification with activated carbon, and a purification process with an adsorption resin.

(3) Securing Purity for Commercialization of Ferulic Acid Through Crystallization Method Ferulic acid was subjected to crystallization to secure a purity of 98% or higher, which is the commercial purity, using the fraction of the above detached fractions (20% ethanol and 30% ethanol). Crystallization was performed in the order of 1) condensation of the detached fractions (10-fold), 2) hot-water dissolution of precipitates (100 mL), 3) proceeding with crystallization by temperature control (lowering temperature), and 4) recovery of ferulic acid crystals.

As a result of performing this procedure, the recovery rate of the input solution to crystals by condensation precipitation was 81.8%, and the recovery rate of crystallization rate after the hot-water dissolution was evaluated to be at the level of 88%. The purity of the final ferulic acid was 98.7%, and was thus recovered in a commercial quality, and the final yield of the crystallization process was 72% (Table 7, FIG. 6).

TABLE 7

| Category | | Result | |
|---|---|---|---|
| Input Soln. FA | | 280.0 | mg |
| Condensation Precipitation | FA | 229.0 | mg |
| | Recovery rate | 81.8 | % DS |
| Crystallization | FA | 201.6 | mg |

TABLE 7-continued

| Category | | Result | |
|---|---|---|---|
| | Recovery rate | 88.0 | % DS |
| FA Yield | | 72.0 | % DS |
| FA Purity | | 98.7 | % |

The final purity of ferulic acid obtained through the above-described process was 98.7%, which is similar to the level of the standard product (99%), and ferulic acid was produced as a product suitable for the 98% purity level of ferulic acid which is currently commercialized.

Figure 6A:
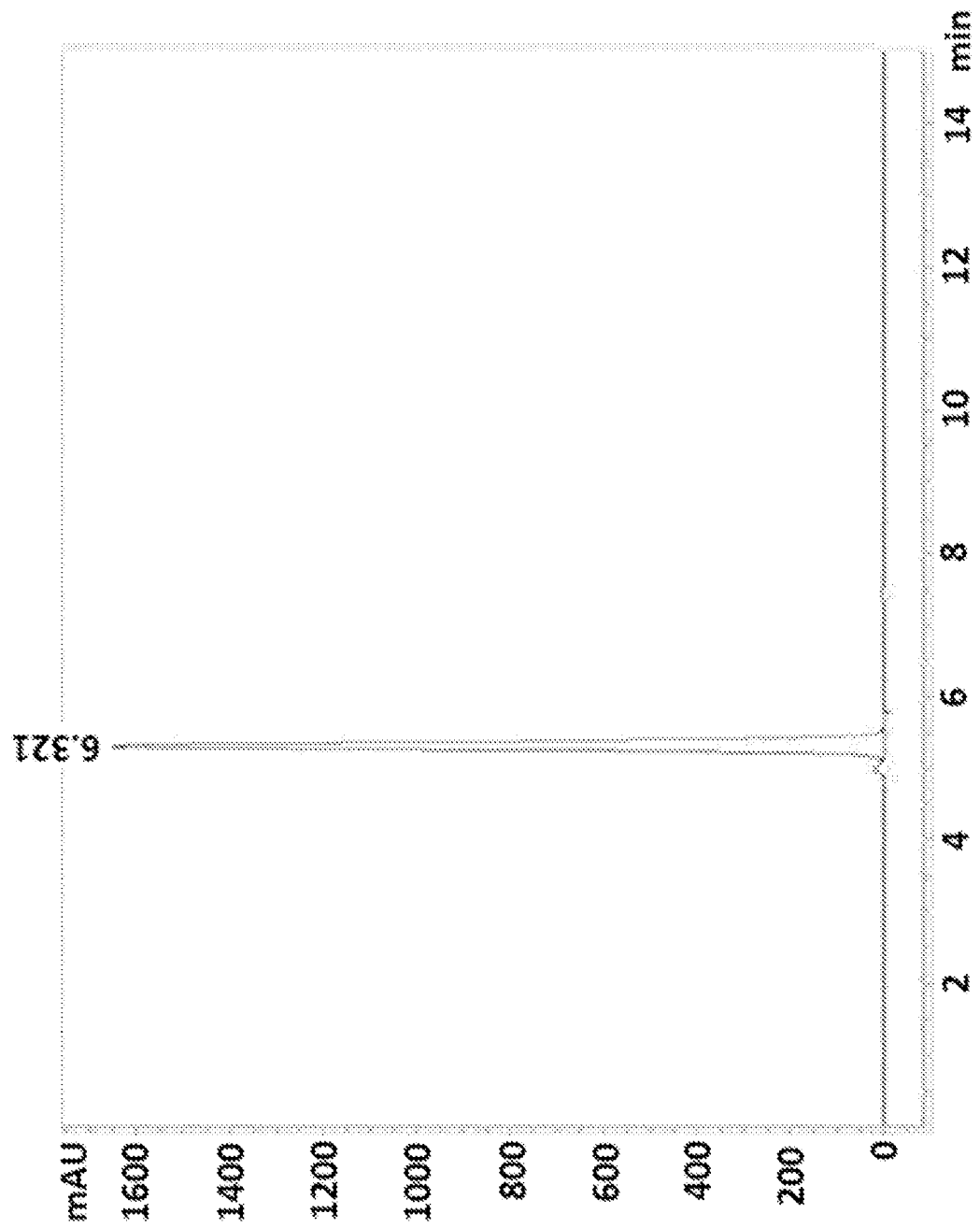
FIGS. 6A and 6B show a purity evaluation of ferulic acid by HPLC analysis.
Figure 6B:
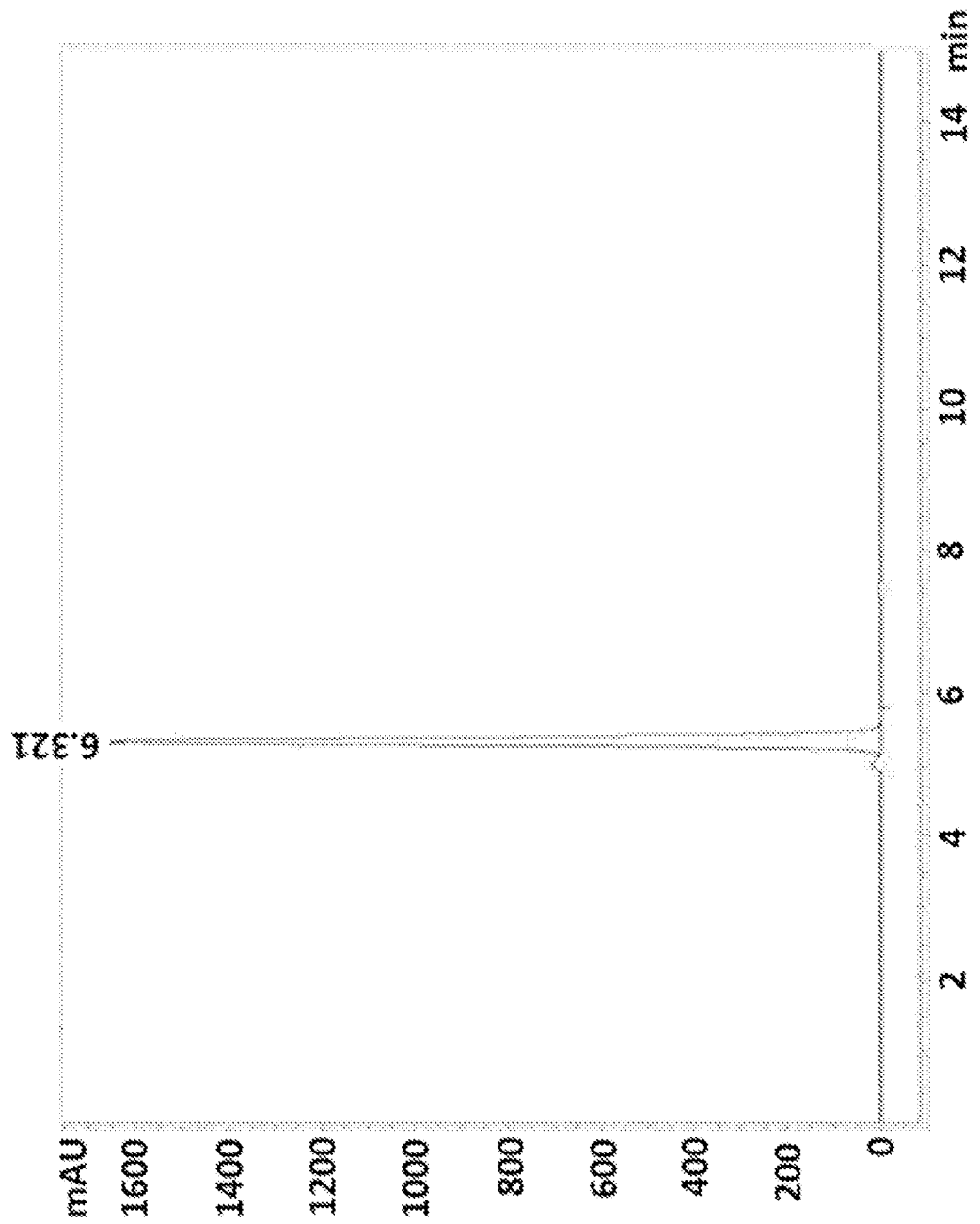

The File information for the LC chromatograms in FIGS. 6A and 6B are provided below:

FIG. 6A
File Information

| | |
|---|---|
| LC-File | 041-0101.D |
| File Path | D:\CHEM32\1\DATA\FA131001\DEF_LC 2013-10-01 17-55-41\ |
| Date | 1 Oct. 2013, 17:55:57 |
| Sample | STD_FA |
| Sample Info | |
| Barcode | |
| Operator | CHK |
| Method | FERULIC ACID(ORZYA).M |
| Analysis Time | 14.993 min |
| Sample Rate | 0.0067 min (0.402 sec). 2250 datapoints |

| # | Time | Area | Height | Width | Area % | Symmetry |
|---|---|---|---|---|---|---|
| 1 | 5.321 | 13425 | 1691.7 | 0.1266 | 100.000 | 0.878 |

FIG. 6B
File Information

| | |
|---|---|
| LC-File | 041-0101.D |
| File Path | C:\CHEM32\1\DATA\FA131001\DEF_LC 2013-10-01 19-12-41\ |
| Date | 1 Oct. 2013, 19:12:56 |
| Sample | FA_S |
| Sample Info | |
| Barcode | |
| Operator | CHK |
| Method | FERULIC ACID(ORZYA).M |
| Analysis Time | 14.993 min |
| Sample Rate | 0.0067 min (0.402 sec). 2250 datapoints |

| # | Time | Area | Height | Width | Area % | Symmetry |
|---|---|---|---|---|---|---|
| 1 | 5.321 | 13226.9 | 1675.7 | 0.1241 | 100.000 | 0.915 |

Based on these results, the present inventors have invented a process for efficient mass production of ferulic acid, which is a high value-added material that has conventionally been produced using materials refined from original oil (i.e., a by-product produced from the existing rice bran oil preparation) as a raw material in the presence of various solvents (IPA, hexane, ethanol, etc.), using corn brans, which are an economical raw material enabling mass production, through simplified methods of extraction, purification, and crystallization enabling high yield.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

What is claimed is:

1. A method for preparing ferulic acid, comprising:
   (a) reacting corn brans with an alkali solution to obtain a crude extract comprising ferulic acid;
   (b) removing starch from the crude extract obtained in step (a) through an enzyme reaction in which the crude extract is reacted with α-amylase, glucoamylase, or both α-amylase and glucoamylase; and
   (c) washing the extraction residue of corn brans.

2. The method of claim 1, wherein the alkali solution is sodium hydroxide or potassium hydroxide.

3. The method of claim 2, wherein the alkali solution is at a concentration of 0.5% (w/w) to 1.5% (w/w).

4. The method of claim 1, wherein the reaction is performed for 1 to 24 hours.

5. The method of claim 1, wherein the solid-liquid ratio between the corn brans and the alkali solution is in the range of 1:3 to 1:15.

6. The method of claim 1, wherein the reaction is performed at 60° C. to 100° C.

7. The method of claim 1, wherein step (a) further comprises filtering the crude extract obtained therein to remove solids.

8. The method of claim 1, wherein the crude extract obtained in step (a) is reacted with α amylase and glucoamylase.

9. The method of claim 1, further comprising (d) separating and purifying ferulic acid.

10. The method of claim 9, wherein the separation and purification comprises a primary purification process using activated carbon and a secondary purification process using adsorption resin.

11. The method of claim 10, wherein the activated carbon is granular activated carbon or powdered activated carbon.

12. The method of claim 10, wherein the primary purification process comprises (i) adsorption of activated carbon, (ii) hot-water washing of activated carbon, and (iii) desorption of ferulic acid within activated carbon.

13. The method of claim 12, wherein the desorption is performed using an alkali solvent.

14. The method of claim 13, wherein the alkali solvent is sodium hydroxide or potassium hydroxide.

15. The method of claim 13, wherein the alkali solvent is contained at a concentration of 0.01% (w/w) to 0.5% (w/w).

16. The method of claim 12, wherein the primary purification process further comprises adjusting the pH of the process solution to 3 to 4, which is detached through the desorption of ferulic acid, so as to remove impurities.

17. The method of claim 10, wherein the adsorption resin is a polystyrenic resin.

18. The method of claim 10, wherein the secondary purification process comprises adsorbing the process solution obtained in the primary purification process to an adsorption resin and desorbing the process solution therefrom.

19. The method of claim 9, further comprising crystallizing the ferulic acid which is separated and purified.

* * * * *